(12) United States Patent
Kimura et al.

(10) Patent No.: US 8,268,824 B2
(45) Date of Patent: Sep. 18, 2012

(54) THERAPEUTIC AGENT FOR CORNEAL DISEASE

(75) Inventors: Takahito Kimura, Toyama (JP); Shigeto Fujishita, Toyama (JP); Hiroyoshi Kawada, Toyama (JP)

(73) Assignee: Teika Pharmaceutical Co., Ltd., Toyama-shi (JP)

( * ) Notice: Subject to any disclaimer, the term of this patent is extended or adjusted under 35 U.S.C. 154(b) by 0 days.

(21) Appl. No.: 12/685,860

(22) Filed: Jan. 12, 2010

(65) Prior Publication Data

US 2010/0113456 A1 May 6, 2010

Related U.S. Application Data

(62) Division of application No. 11/912,899, filed as application No. PCT/JP2006/308803 on Apr. 27, 2006, now abandoned.

(30) Foreign Application Priority Data

Apr. 27, 2005 (JP) ................................. 2005-129450

(51) Int. Cl.
*A61K 31/53* (2006.01)
(52) U.S. Cl. ........................................ 514/245; 514/912
(58) Field of Classification Search .................. 514/245, 514/912

See application file for complete search history.

(56) References Cited

U.S. PATENT DOCUMENTS

| 6,150,362 A | 11/2000 | Henkin et al. |
| 2009/0247600 A1 | 10/2009 | Kimura et al. |

FOREIGN PATENT DOCUMENTS

| JP | 9-194363 | 7/1997 |
| JP | 2002-255826 | 9/2002 |
| WO | 96 32945 | 10/1996 |
| WO | 2005 026132 | 3/2005 |

OTHER PUBLICATIONS

U.S. Appl. No. 12/828,420, filed Jul. 1, 2010, Kimura, et al.
Ren, Christine J., et al., "Irsogladine Maleate Inhibits Angiogenesis in Wild-Type and Plasminogen Activator-Deficient Mice", Journal of surgical Research, vol. 77, No. 2. p. 126, 1998.
Office Action issued Feb. 8, 2011, in Japan Patent Application No. 2005-129450 (with English-language Translation).
Yutaka Mizushima, et al., "Konnichi no chiryouyaku (modern medications)", 1999, pp. 648-649 (with English-language Translation).
European Search Report dated May 31, 2012 which corresponds to Euruopean Application No. 06 745 731.7.
Akiko Mera Kuroki, et al., "Inhibition of Experimental Choroidal Neovascularization by Irsogladine, an Anti-Gastric Ulcer Agent", Ophthalmic Research, vol. 35, No. 3, May 1, 2003, pp. 137-142.
Takashi Furushima, et al., "Suppression of Endothelial Cells in Diabetic Retinopathy by Systemic Irsogladine", Japanese Journal of Clinical Ophthalmology, vol. 51, No. 5, Jan. 1, 1997, pp. 919-922.

*Primary Examiner* — Zohreh Fay
(74) *Attorney, Agent, or Firm* — Oblon, Spivak, McClelland, Maier & Neustadt, L.L.P.

(57) ABSTRACT

A therapeutic agent for a corneal disease comprising irsogladine or a salt thereof as an active ingredient. The purpose is to find a substance capable of effectively treating/ameliorating a corneal disease which has been increased in the number of cases thereof in recent years and to provide a therapeutic agent for a corneal disease comprising the substance as an active ingredient.

13 Claims, No Drawings

THERAPEUTIC AGENT FOR CORNEAL DISEASE

CROSS-REFERENCE TO RELATED APPLICATIONS

This application is a divisional application of U.S. Ser. No. 11/912,899 filed Oct. 29, 2007, abandoned, which is a 371 of PCT/JP2006/308803 filed Apr. 27, 2006 and claims the benefit of JP 2005-129450 filed Apr. 27, 2005.

TECHNICAL FIELD

The present invention relates to a therapeutic agent for a corneal disease, and more particularly, it relates to a therapeutic agent for a corneal disease applicable to a disorder in the anterior epithelium of cornea, particularly in a formulation of ophthalmic solutions.

BACKGROUND ART

Disorder in the anterior epithelium of cornea can be classified roughly into 4 types, that is, (1) one caused by an inflammation such as infection, (2) hereditary disease, (3) exogenous physical injury and chemical injury caused by chemicals, and (4) nutritional disorder.

Among them, there is a tendency for corneal diseases to increase in recent years due to physical injury accompanied by lacrimal hyposecretion (so-called dry-eye) with the spread of personal computers and contact lens, and those caused by pollinosis, particularly disorder in the anterior epithelium; thus, a drug effective to corneal diseases or disorders in the anterior epithelium of cornea has been demanded.

As drugs recently used in treatment of corneal diseases, artificial tears containing a visco-elastic material such as hyaluronic acid or chondroitin sulfate is known, of which the water-retention effect mainly promotes a cure. There is a limitation, however, in their therapeutic effect, and further it could not be said that they fundamentally cure the corneal disease. A quite new therapeutic agent has been demanded, accordingly.

DISCLOSURE OF INVENTION

Problems to be Solved by the Invention

It is an object of the present invention to find out a drug which is capable of effectively treating and improving a corneal disease increasing in recent years and to provide a therapeutic agent comprising it as an active ingredient.

Means for Solving the Problems

The present inventors have searched for a variety of drugs which have a therapeutic effect on corneal diseases and found that irsogladine maleate, which has widely been used as a medicament for internal application in treatment of gastric ulcer or gastric mucosal lesion, has an excellent therapeutic effect on corneal diseases. The invention was thus completed.

That is, the present invention provides a therapeutic agent for a corneal disease which comprises irsogladine or a salt thereof as an active ingredient.

The present invention also provides a therapeutic agent for a corneal disease as mentioned above which is in a formulation of ophthalmic solutions and which is particularly applicable to disorders in the anterior epithelium of cornea.

Effect of the Invention

The therapeutic agent of a corneal disease of the present invention has an effect of significantly promoting a cure of corneal diseases, particularly cure of disorders in the anterior epithelium of cornea.

BEST MODE FOR CARRYING OUT THE INVENTION

The corneal disease in the present invention indicates conditions of injured cornea caused by various factors, specifically including keratitis caused by physical/chemical irritation, allergy, bacteria/fungi/virus infections, etc., as well as corneal ulcer, abrasion of the anterior epithelium of cornea (corneal erosion), edema of the anterior epithelium of cornea, corneal burn, corneal corrosion by chemicals, dry-eye, and the like.

The therapeutic agent for a corneal disease of the invention comprises irsogladine or a salt thereof as an active ingredient. Irsoglandine and salts thereof as active ingredients are drugs having an anti-ulcer effect, one of which irsogladine maleate (2,4-diamino-6-(2,5-dichlorophenyl)-1,3,5-triazine maleate) has widely been used as an internal formulation in treatment of gastric ulcer or gastric mucosal lesion. It has not yet been known, however, that the ingredient is effective as a therapeutic agent for a corneal disease, particularly in treatment of a disorder of the anterior epithelium of cornea.

In the therapeutic agent for a corneal disease of the present invention, the content of irsogladine or salt thereof is usually, for example, when irsogladine maleate is used in a liquid preparation such as ophthalmic solution or eyewash, preferably 0.01 w/v % to 3 w/v %, more preferably 0.05 w/v % to 1 w/v %, and most particularly 0.1 w/v % to 0.5 w/v %.

The therapeutic agent for a corneal disease of the present invention can be formulated into an optional formulation which can be applied to the cornea, and it is desired to usually provide as a form of ophthalmic solution, eyewash, ophthalmic ointment, and the like, in particular as a form of ophthalmic solution.

For example, when the therapeutic agent for a corneal disease of the present invention is provided as an ophthalmic solution, it is possible to employ in addition to the active ingredient irsogladine or a salt thereof a variety of optional ingredients including buffer, tonicity agent, solubilizer, surfactant, stabilizer, preservative, pH adjuster, and the like.

The optional ingredients are exemplified specifically by buffer such as potassium dihydrogen phosphate, sodium hydrogen phosphate, boric acid, sodium borate, sodium citrate, sodium acetate, monoethanolamine, trometamol, and the like; tonicity agent such as sodium chloride, potassium chloride, glycerin, glucose, and the like; solubilizer such as ethanol, castor oil, and the like; surfactant such as polysorbate 80, polyoxyethylene hardened castor oil, and the like; stabilizer such as sodium ethylenediaminetetraacetate and the like; preservative such as benzalkonium chloride, benzethonium chloride, chlorobutanol, benzyl alcohol, and the like, and pH adjuster such as hydrochloric acid, sodium hydroxide, and the like.

In addition, the therapeutic agent for a corneal disease of the present invention can be simultaneously used with another type of therapeutic ingredients for a corneal disease of which the action mechanism is considered to be different in order to enhance additively or synergistically the therapeutic effect. The another type of therapeutic ingredients for a corneal disease includes, for example, hyaluronic acid or its salt or chondroitin sulfate or its salt. Those ingredients may be combined with irsogladine or a salt thereof, or may be separately formulated into a single formulation for treatment of a corneal disease so as to use concomitantly.

The therapeutic agent for a corneal disease thus obtained may be applied appropriately to the cornea depending on the type or severity of a corneal disease. In general, a dose of about 0.01 to 0.1 mL for one eye may be administered 3 to 6 times per day.

EXAMPLES

The following Examples and Test Example will illustrate the present invention in more detail. The therapeutic agent for a corneal disease of the invention, however, is not limited by Examples described below, and of course it may be modified in various ways within the scope of the invention as far as the modification does not depart from the gist of the invention.

Example 1

Therapeutic Agent-1 for a Corneal Disease

| (Component) | |
| --- | --- |
| Irsogladine maleate | 0.1 g |
| Polysorbate 80 | 2 g |
| Ethanol | 5 g |
| Physiological saline | Balance to total 100 mL |

(Method of Preparation)

Irsogladine maleate was dissolved in ethanol, and polysorbate 80 was added to the solution. Then, physiological saline was added to the mixture to obtain 100 mL of a therapeutic agent for a corneal disease as an ophthalmic solution.

Example 2

Therapeutic Agent-2 for a Corneal Disease

| (Component) | |
| --- | --- |
| Irsogladine maleate | 0.3 g |
| Polysorbate 80 | 5 g |
| Ethanol | 5 g |
| Physiological saline | Balance to total 100 mL |

(Method of Preparation)

Irsogladine maleate was dissolved in ethanol, and polysorbate 80 was added to the solution. Then, physiological saline was added to the mixture to obtain 100 mL of a therapeutic agent for a corneal disease as an ophthalmic solution.

Example 3

Oily-Based Ophthalmic Solution

| (Component) | |
| --- | --- |
| Irsogladine maleate | 0.3 g |
| Castor oil | 99.7 g |

(Method of Preparation)

Irsogladine maleate was mixed with castor oil in a conventional manner to obtain a therapeutic agent for a corneal disease as an oily-based ophthalmic solution.

Example 4

Ophthalmic ointment

| (Component) | |
| --- | --- |
| Irsogladine maleate | 0.3 g |
| Liquid paraffin | 30.0 g |
| Vaseline | 69.7 g |

(Method of Preparation)

Irsogladine maleate was added to a mixture of liquid paraffin and vaseline, and the mixture thus obtained was admixed with stirring in a conventional manner to obtain a therapeutic agent for a corneal disease as an ophthalmic ointment.

Test Example (1) Formation of Wound

A matured white rabbit (about 2 kg of body weight) was anesthetized with pentobarbital sodium (0.4 mL/kg) injected into auricular vein; the eyelid was widely opened with an eye speculum, to which 30 µL of benoxil ophthalmic solution was applied to anesthetize the eye surface. Then, a membrane filter (6 mm in diameter) moistened with n-heptanol was placed at the center of rabbit's cornea for one minute to yield corneal injury. After the filter was removed, the eye was washed well with sterilized physiological saline.

In addition, immediately after formation of the wounds, there was no significant difference among groups in the area of wounds; this was confirmed in the same procedure as in observation of cure as mentioned below.

(2) Application of the Preparation

At three, four and five hours after formation of the wound, 100 µL of the therapeutic agents for corneal disease (ophthalmic solution) prepared in Example 1 and Example 2, respectively, were applied to the eye. In this test, physiological saline containing 2% ethanol and 2% polysorbate 80 was used as a control for Example 1, and physiological saline containing 5% ethanol and 2% polysorbate 80 was used as a control for Example 2.

(3) Staining and Observation of Cure

At 24 hours after formation of the wound, 1% aqueous fluorescein solution (50 µL) was applied to the eye for staining. After that, excess fluorescein was washed out with sterilized physiological saline. Subsequently, the cornea was photographed with a digital camera fitted to a photo-slit lamp to observe the status of cure of the wound.

(4) Evaluation

In each experiment, immediately after and 24 hours after the application, the stained area was measured using a image processing software with a label width (5 mm) of eye speculum as a standard, and this was regarded as a wound area. From those results, the cure rate was calculated according to the following formula.

Cure rate (%)=[1-($S_B$/$S_A$)]×100

$S_A$: wound area immediately after formation of wound
$S_B$: wound area after application of the preparation Table 1 shows the test results in the therapeutic agent-1 for a corneal disease, and Table 2 shows the test results in the therapeutic agent-2 for a corneal disease, respectively.

TABLE 1

|  | Cure Rate (Mean ± S.E. (n = 3)) |
| --- | --- |
| Control | 33.59 ± 4.93 |
| Therapeutic agent-1 | 56.04 ± 0.82* | t-test *P < 0.05 vs Control

TABLE 2

|  | Cure Rate (Mean ± S.E. (n = 6)) |
| --- | --- |
| Control | 47.97 ± 3.30 |
| Therapeutic agent-2 | 58.22 ± 2.99* | t-test *P < 0.05 vs Control

As mentioned above, it was shown that the therapeutic agent for a corneal disease in the present invention has a potent curative effect to a disorder in the anterior epithelium of cornea.

INDUSTRIAL APPLICABILITY

The pharmaceutical preparation of the present invention comprising irsogladine maleate as an active ingredient has an effect significantly promoting a cure of a corneal disease, particularly, a cure of a disorder in the anterior epithelium of cornea. The pharmaceutical preparation, accordingly, is effective as a novel therapeutic agent for a corneal disease.

The invention claimed is:

1. A method of treating an injured cornea, the method comprising administering to a patient in need thereof, an effective amount of irsogladine or a salt thereof.

2. The method of claim 1, wherein irsogladine or the salt thereof is administered in an ophthalmic solution or eyewash.

3. The method of claim 1, wherein an irsogladine salt is administered.

4. The method of claim 1, wherein the salt is a maleate salt.

5. The method of claim 2, wherein irsogladine or the salt thereof is present in an amount of 0.01 w/v % to 3 w/v %.

6. The method of claim 2, wherein irsogladine or the salt thereof is present in an amount of 0.05 w/v % to 1 w/v %.

7. The method of claim 2, wherein irsogladine or the salt thereof is present in an amount of 0.1 w/v % to 0.5 w/v %.

8. The method of claim 2, wherein the ophthalmic solution or eyewash further comprises one or more of a buffer, a tonicity agent, a solubilizer, a surfactant, a stabilizer, a preservative, and a pH adjuster.

9. The method of claim 1, further comprising administering hyaluronic acid, chondroitin sulfate, a salt thereof, or a combination thereof.

10. The method of claim 1, wherein irsogladine or the salt thereof is administered in a dose of 0.01 to 0.1 mL for one eye.

11. The method of claim 10, wherein irsogladine or the salt thereof is administered from 3 to 6 times per day.

12. The method of claim 1, wherein irsogladine or the salt thereof is administered from 3 to 6 times per day.

13. The method of claim 1, wherein the injured cornea is caused by keratitis caused by physical irritation, keratitis caused by chemical irritation, allergy, a bacterial infection, a fungal infection, a viral infection, a corneal ulcer, abrasion of the anterior epithelium of the cornea, a corneal burn, a corneal chemical corrosion, or dry-eye.

* * * * *